(12) United States Patent
Koike

(10) Patent No.: US 8,894,613 B2
(45) Date of Patent: Nov. 25, 2014

(54) CATHETER ATTACHMENT AND METHOD

(76) Inventor: Hideo Koike, White Plains, NY (US)

( * ) Notice: Subject to any disclaimer, the term of this patent is extended or adjusted under 35 U.S.C. 154(b) by 0 days.

(21) Appl. No.: 13/011,867

(22) Filed: Jan. 22, 2011

(65) Prior Publication Data

US 2012/0191044 A1 Jul. 26, 2012

(51) Int. Cl.
*A61M 5/32* (2006.01)
*A61M 5/00* (2006.01)
*A61M 25/02* (2006.01)
*A61M 25/01* (2006.01)
*A61M 25/00* (2006.01)

(52) U.S. Cl.
CPC ............ *A61M 25/02* (2013.01); *A61M 25/0111* (2013.01); *A61M 2025/0056* (2013.01); *A61M 2025/0273* (2013.01); *A61M 25/0017* (2013.01)
USPC ............ 604/163; 604/171; 604/180; 604/263

(58) Field of Classification Search
CPC ............ A61M 25/0111; A61M 25/02; A61M 2025/0266; A61M 1/0088; A61M 2025/0273; A61M 2025/0246; A61M 2025/028; A61M 2025/0056; A61M 2209/088; A61M 25/0017; A61M 25/002; Y10S 128/26; Y10S 128/912; A61B 19/081
USPC .................. 604/171, 163, 172, 263, 174, 180
See application file for complete search history.

(56) References Cited

U.S. PATENT DOCUMENTS

| | | | | |
|---|---|---|---|---|
| 3,683,911 A * | 8/1972 | McCormick | .................. | 604/180 |
| 4,327,723 A * | 5/1982 | Frankhouser | .................. | 604/171 |
| 4,327,735 A * | 5/1982 | Hampson | ...................... | 604/171 |
| 4,392,853 A * | 7/1983 | Muto | ............................ | 604/171 |
| 4,515,492 A * | 5/1985 | Shan | ............................... | 401/52 |
| 4,551,137 A * | 11/1985 | Osborne | ........................ | 604/171 |
| 4,634,433 A * | 1/1987 | Osborne | ........................ | 604/171 |
| 4,696,296 A * | 9/1987 | Palmer | ..................... | 128/207.16 |
| 4,767,409 A * | 8/1988 | Brooks | ......................... | 604/171 |
| 4,906,232 A * | 3/1990 | Reynolds | ..................... | 604/171 |
| 4,973,314 A * | 11/1990 | Garrett | .......................... | 604/180 |
| 5,059,186 A | 10/1991 | Yamamoto | | |
| 5,125,893 A * | 6/1992 | Dryden | ........................ | 604/500 |
| 5,134,996 A * | 8/1992 | Bell | .......................... | 128/207.14 |
| 5,234,411 A * | 8/1993 | Vaillancourt | ................. | 604/171 |
| 5,261,893 A * | 11/1993 | Zamierowski | ............... | 604/180 |
| 5,269,756 A * | 12/1993 | Dryden | ........................ | 604/171 |
| 5,336,193 A * | 8/1994 | Rom et al. | ..................... | 604/171 |
| 5,354,267 A * | 10/1994 | Niermann et al. | .............. | 604/32 |
| 5,358,495 A * | 10/1994 | Lynn | ............................. | 604/171 |
| 5,490,503 A * | 2/1996 | Hollister | .................. | 128/205.12 |
| 5,598,840 A * | 2/1997 | Iund et al. | ................ | 128/207.14 |
| 5,715,815 A * | 2/1998 | Lorenzen et al. | ........ | 128/207.14 |
| 5,779,687 A * | 7/1998 | Bell et al. | ...................... | 604/265 |
| 5,833,666 A * | 11/1998 | Davis et al. | .................... | 604/180 |
| 6,537,254 B1 * | 3/2003 | Schock et al. | ................ | 604/171 |

(Continued)

*Primary Examiner* — Kevin C Sirmons
*Assistant Examiner* — William Carpenter
(74) *Attorney, Agent, or Firm* — Gorman Law Offices; Robert Gorman

(57) ABSTRACT

An improved catheter attachment apparatus is provided for use in reducing infections associated with a percutaneous medical device, such as a catheter. Such a barrier system can include: a barrier device having a catheter-receiving surface or enclosed tube; and an adhesive composition configured for adhering to skin. The improved catheter attachment apparatus forms a physical barrier against microbes at or adjacent to an incision in the skin where the catheter is percutaneously inserted through the skin, yet permits ready access by medical personnel for readjusting the catheter and/or any sutures used therewith.

5 Claims, 5 Drawing Sheets

(56) References Cited

U.S. PATENT DOCUMENTS

| | | | |
|---|---|---|---|
| 6,569,121 B1 * | 5/2003 | Purow et al. | 604/174 |
| 6,949,114 B2 | 9/2005 | Milo et al. | |
| 7,117,869 B2 * | 10/2006 | Heaton et al. | 128/897 |
| 7,625,346 B2 | 12/2009 | Grigoryants et al. | |
| 7,662,146 B2 * | 2/2010 | House | 604/544 |
| 7,758,514 B2 | 7/2010 | Grigoryants et al. | |
| D622,375 S * | 8/2010 | Tsuruoka et al. | D24/127 |
| 7,988,673 B2 * | 8/2011 | Wright et al. | 604/174 |
| 2004/0106912 A1 | 6/2004 | Rosinskaya et al. | |
| 2007/0224243 A1 | 9/2007 | Bayston | |
| 2008/0279907 A1 | 11/2008 | Ash et al. | |
| 2008/0300578 A1 * | 12/2008 | Freedman | 604/543 |
| 2009/0157000 A1 | 6/2009 | Waller | |
| 2010/0010086 A1 | 1/2010 | Ash et al. | |
| 2010/0082003 A1 | 4/2010 | Hunter et al. | |
| 2010/0106102 A1 | 4/2010 | Ziebol et al. | |
| 2010/0106103 A1 | 4/2010 | Ziebol et al. | |

\* cited by examiner

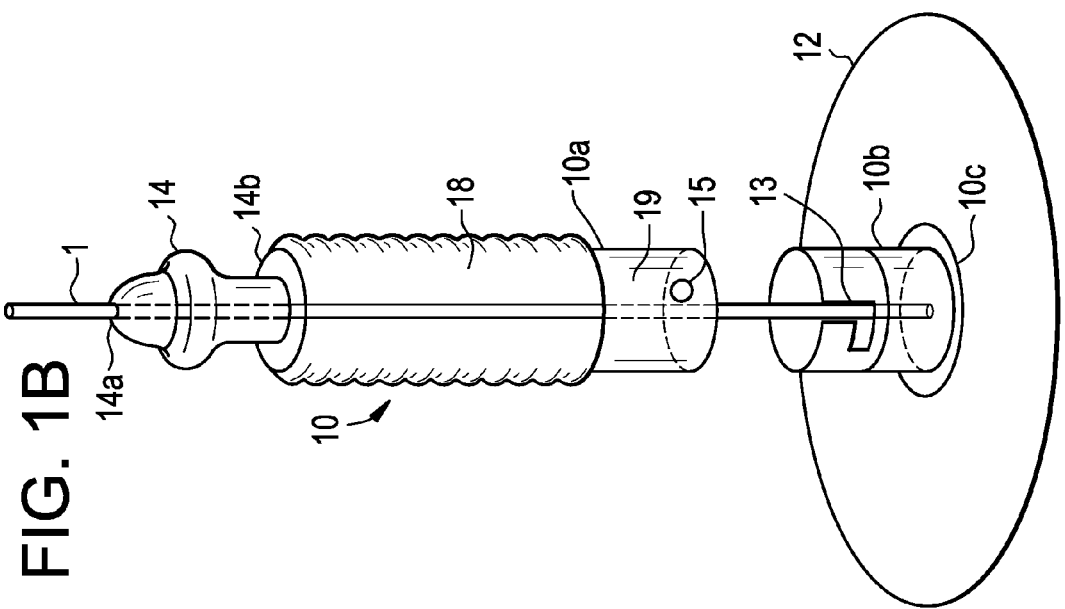
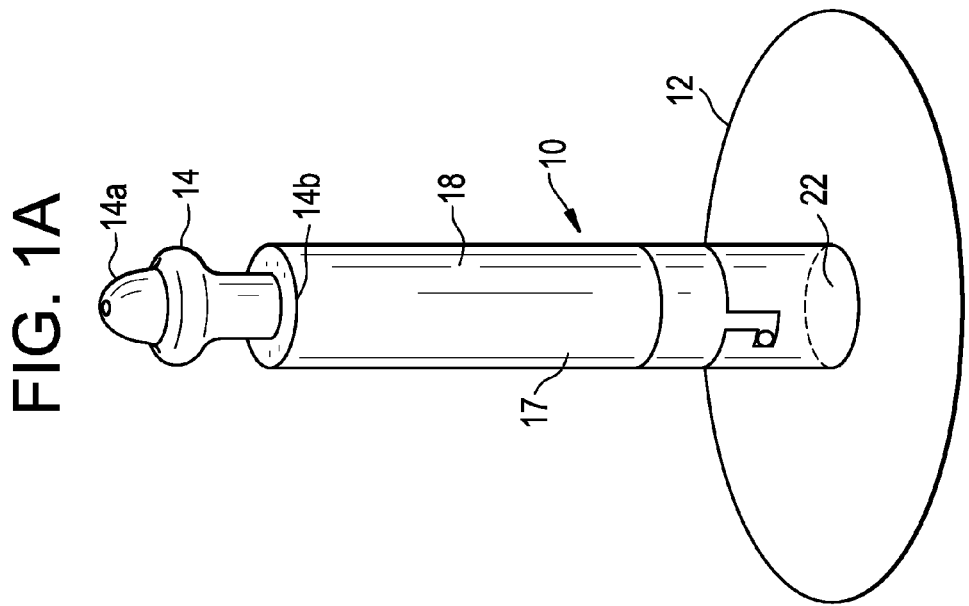

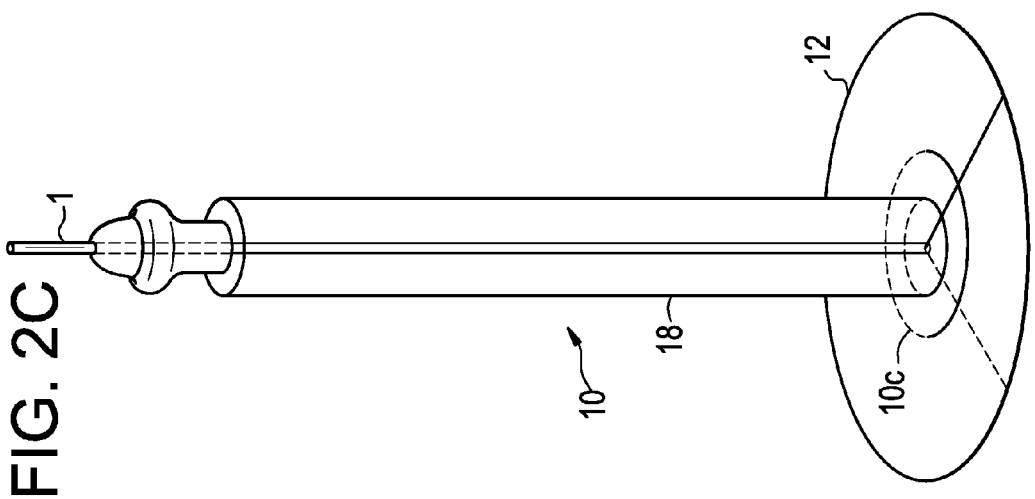
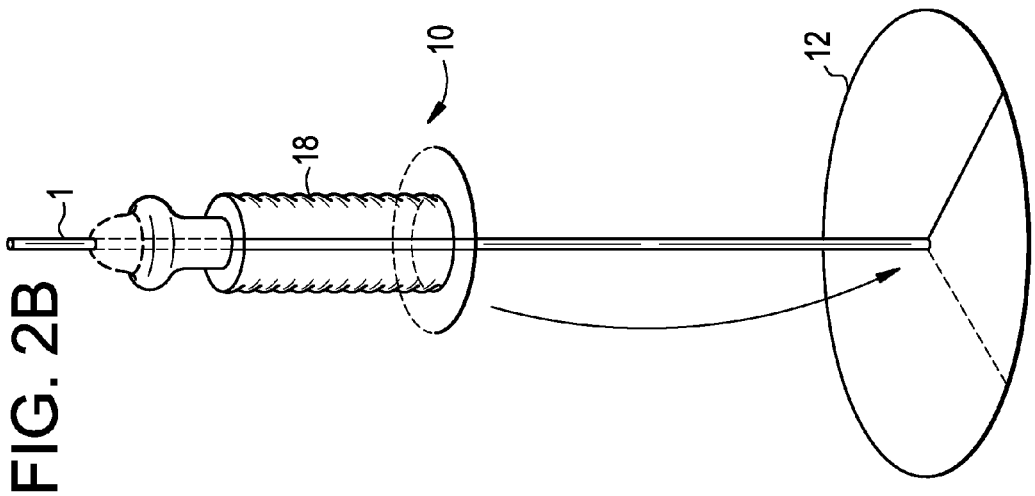
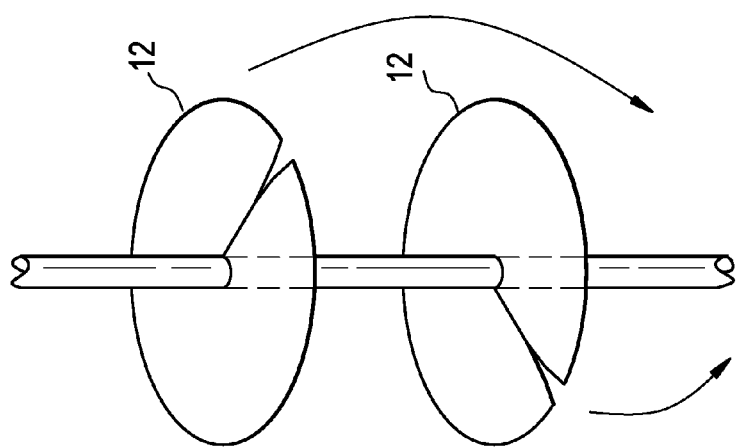

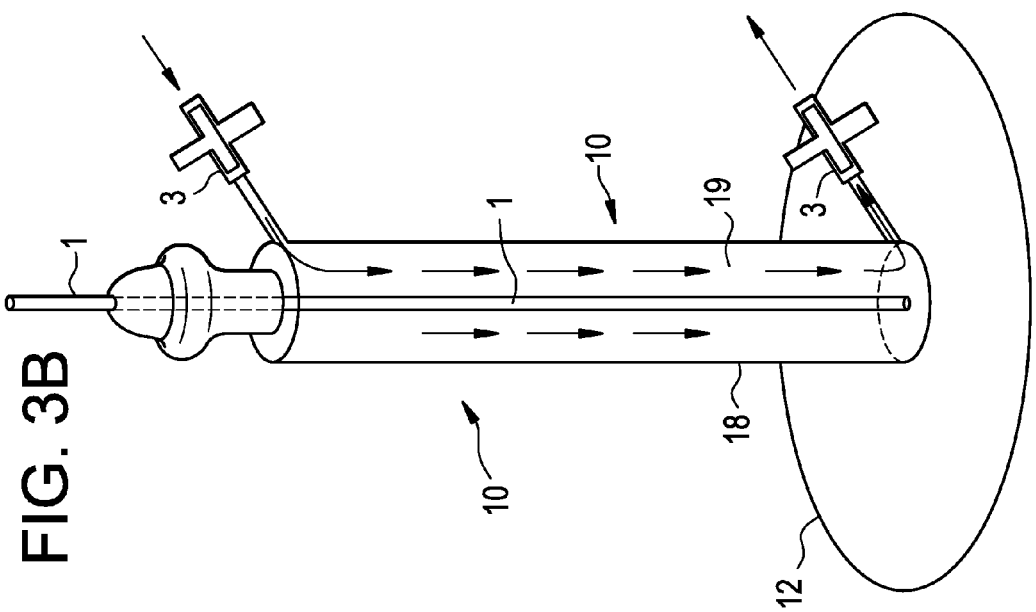
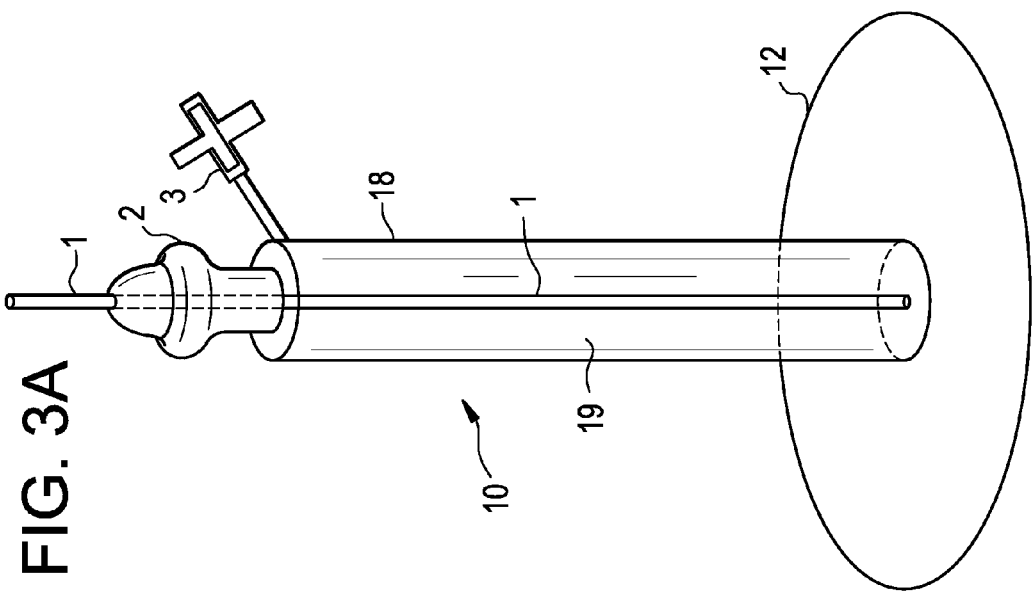

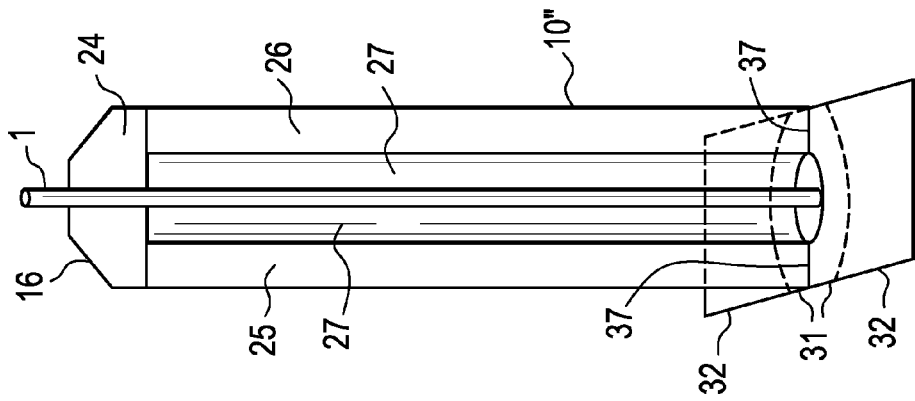
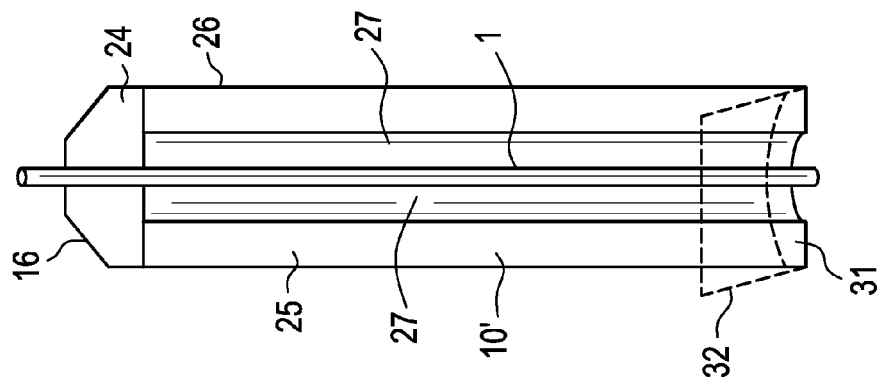

CATHETER ATTACHMENT AND METHOD

BACKGROUND OF THE INVENTION

1. Field of the Invention

The present invention relates generally to medical instruments and catheters, and more particularly to improved catheters which physically block access to catheter puncture sites by infection-causing microbes, and which are structured so as to provide for the ease of use and administration thereof by medical professionals.

2. Brief Description of the Prior Art

Infections resulting from catheters are responsible for numerous treatment complications, and in some cases, deaths of patients. This treatment factor is particularly troublesome, given the extensive usage of catheters. Normally, catheter infections are typically caused by contamination of the catheter hub, with progression of the bacteria or other microbes down the extra- and intra-luminal surface of the catheter, where they colonize on the skin, with subsequent progression of the microbes down the extra- or intra-luminal surface and into the bloodstream, resulting in localized and/or systemic infections in patients. Methods to reduce the number of catheter-related infections (CRIs) have included: strict insertion guidelines, sterile catheter materials, and topical antibiotic ointments applied at the catheter insertion site, chlorohexedine impregnated sponges which encircle the catheter at the catheter-skin interface, etc. These interventions have demonstrated varying degrees of efficacy. Despite these interventions, CRIs still remain a problem, particularly given the recent prevalence of MRSA-type infections which do not respond well to such anti-biotic treatments.

One attempt to preventing CRIs is disclosed in US Patent Publication Number 2009/0157000 to Waller, which purportedly gives some protection onto and around catheter insertion sites. However, this approach is deficient because it is limited in the extent of the physical barriers provided therewith. In particular, catheters are frequently manipulated by medical personnel such as nurses and physicians with bare hands or while wearing non-sterile gloves during the course of needed readjustments to catheters and insertion sites. Any such handling on the exposed portion of the catheter can still infect the surfaces of the catheter materials and lead to migration of infectious microbes into the insertion site. Moreover, approaches such as that proposed above can interfere with the necessary manipulating of catheters by medical professionals, especially because they are not "open access" in structure. In other cases, such as that seen with bladder catheters, the approach described by Waller may not even be used with various types of catheters, especially when using bladder catheters. The lack of comprehensive physical barriers in Waller is even more dangerous, because types of catheters like bladder catheter (or other types of catheters that may be placed in pelvic regions) are often soiled with stool because given their proximity to excretive functional areas on the human body. The deficiencies of Waller are further compounded by the difficulty medical professional would encounter when removing the protective barrier during necessary catheter adjustments and other procedures which require access to the entire length of the catheter.

Therefore, it would be beneficial to have an improved device and/or method of reducing catheter infection rates, especially one which more comprehensive protective coverage of catheter surface areas up to and including most of the whole catheter, such that the covered portion of the catheter therein remains sterile no matter what the type of catheter or the physical application thereof on a patient. It would also be advantageous to provide for an approach which not only defeats the surface area migration of microbes (including MRSA resistant strains thereof) into suture sites, but also is has the ability to provide, if desired, for ease of removal by medical professionals when adjusting catheters (and the maintenance of the sterility thereof during said removal), and might also provide for supplemental protections such site irrigation and/or sterility maintenance through inert gas infusion therein.

SUMMARY OF THE INVENTION

The present invention is distinguished over the prior art in general by a providing a device that includes a barrier system for reducing infections associated with a catheter in such a way so as to provide for comprehensive protective coverage of catheter surface areas up to and including most of the whole catheter so as to defeats the surface area migration of microbes (including MRSA resistant strains thereof) into suture sites, yet which also provides for ease of removal by medical professionals when adjusting catheters, and provides for supplemental protections such site irrigation and/or sterility maintenance through inert gas infusion.

It is therefore an object of the present invention to provide an improved catheter, which in one embodiment, can include: a barrier device having a skin-contacting surface and a catheter-receiving module; and a variety of possible adhesive structures configured for adhering to skin, the barrier device, and/or the catheter so as to form a barrier at or adjacent to an incision in the skin where the catheter is percutaneously inserted through the skin. The barrier device can include an open-access conduit configured to receive the catheter. Alternatively, the catheter may optionally provide supplemental structure for site irrigation and/or sterility maintenance through inert gas infusion.

These and other embodiments and features of the present invention will become more fully apparent from the following description and appended claims, or may be learned by the practice of the invention as set forth hereinafter.

BRIEF DESCRIPTION OF THE DRAWINGS

FIGS. 1a-1b are side views in partial cross section showing locked (1a) and unlocked (2b) an illustration of a rigid or preferably, flexible lock-tight tube version of the improved catheter attachment in accordance with different embodiments of the present invention, with a disc based adhesive structure at the bottom of the tube.

FIGS. 2a-2c are side views in partial cross section showing an integral tube version of the improved catheter attachment in accordance with different embodiments of the present invention, with a disc based adhesive structure at the bottom of the tube.

FIGS. 3a-b are side views in partial cross section showing either tube version of the improved catheter attachment in accordance with different embodiments of the present invention, with either adhesive structure (2a) for positioning at the bottom of the tube, and an inert gas filling attachment and structure (3a), or alternatively, an irrigation attachment and structure (3b).

FIGS. 5a-b are a perspective and a side view in partial cross section showing a non-tube version of the improved catheter attachment in accordance with an alternative embodiment of the present invention, with a segmented adhesive wrap formed from two matching adhesive strips for enveloping and sealing off and longitudinally around a length of a lumen of a catheter and for attaching the same to skin and sealing off an insertion site by forming a microbial-impervious physical barrier.

DESCRIPTION OF THE PREFERRED EMBODIMENTS

Figure 4:
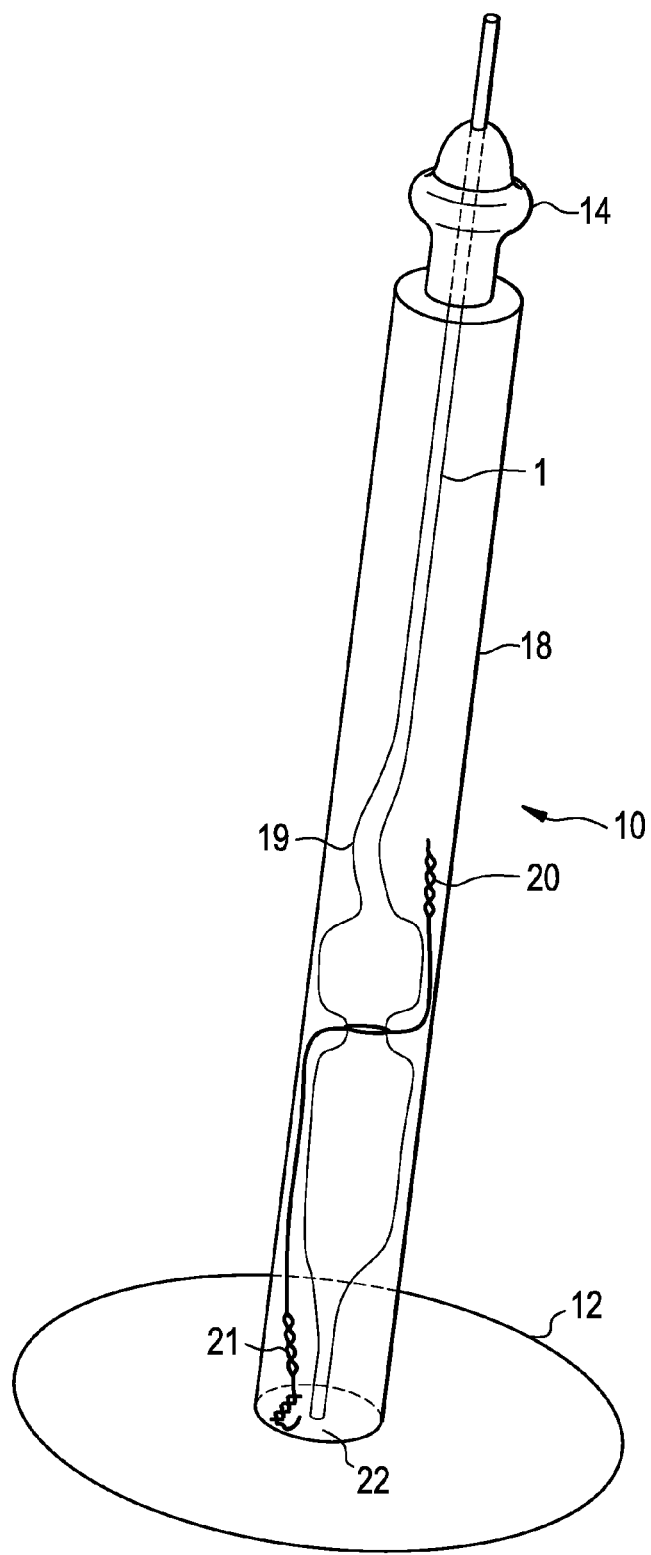
FIG. 4 is a side view in partial cross section showing either tube version of the improved catheter attachment in accordance with the present invention, with an anchoring suture structure and application therein.

At its broadest level, the present invention is directed to an improved catheter attachment apparatus for reducing infections associated with a catheter, wherein the improved catheter attachment apparatus comprises: an elongated tube structure having a bottom end and a top end and a tube conduit extending from an opening at the top end, to an opening at said bottom end for receiving a length of a lumen of a catheter, with a flange base at said bottom end; a seal attached to said top end of the elongated tube structure, the seal being configured for receiving the lumen of the catheter and so as to form a physical barrier to microbial entry at the top end of said elongated tube structure, the seal further comprising: a narrowed opening at a top end of the seal for receiving the lumen of the catheter and for sealable engagement with the lumen of said catheter thereby; a widened opening at a bottom end of the seal, said widened opening being in concentric frictional engagement with the opening at the top end of the elongated tube structure; and a seal conduit, the seal conduit extending from the narrowed opening, to the widened opening, for passing through of the lumen of the catheter from the narrowed opening to the widened opening, and for passing through of the lumen of the catheter at the opening at the top end of said elongated tube structure, into the elongated tube structure; an adhesive structure for adhering to set flange base at the bottom end of the elongated tube structure and for adhering to skin, the adhesive structure being further configured so as to form a physical barrier to microbial entry at said bottom end of the elongated tube structure. Also, the improved catheter attachment apparatus may also include at least one of the following structural features chosen from the group comprising a seal gas chamber, irrigation fitment, or anchoring suture fitment, as shall be described herein, and may have an elongated tube structure that is formed from a flexible, collapsible accordion profiled plastic tubing. In one embodiment, the improved catheter attachment apparatus has an elongated tube structure that is formed from a single integral tube, or alternatively, a bifurcated tube that has an upper portion having a locking notch, and a lower portion having a cooperative groove for receiving and locking the locking notch upon frictional concentric engagement of said upper portion concentrically within said lower portion. In one alternative embodiment of the improved catheter attachment apparatus the structure may instead comprise: two elongated, flat adhesive strips with substantially matching profiles for adhering each of the two elongated flat adhesive strips to each other longitudinally about a catheter lumen, the two elongated flat adhesive strips being further provided segmented release liners for sequentially adhering: first, an upper portion of the two elongated flat adhesive strips to each other longitudinally about said lumen of the catheter, and then thereafter, the remaining portions of said two elongated flat adhesive strips to each other; the two elongated, flat adhesive strips being further provided with an additional adhesive structure comprising additionally segmented adhesive release liners for adhering the two elongated flat adhesive strips to skin.

Accordingly, the present invention includes a barrier device, adhesive structure, system having the device and adhesive, and methods of using the device and adhesive that inhibit and/or prevent infections from occurring at or in an insertion site where a medical device (e.g., catheter) penetrates the skin. For example, the insertion site can be from a catheter, needle, or other medical device that is inserted through the skin. Also, the barrier device and adhesive can be used to affix the medical device at a desired position with respect to the insertion site so that the medical device does not move during a medical procedure or during normal patient movement. Affixing the medical device at or in the insertion site can inhibit microbes from migrating into the insertion site by inhibiting the inward and outward slippage of the medical device with respect to the incision (e.g., pistoning). Thus, the device can be applied to skin at or proximal to an insertion site in the skin with the adhesive in order to inhibit and/or prevent infections from occurring and/or propagating at the insertion site.

The device and adhesive structure can cooperate so as to provide a mechanical barrier on the skin at the insertion site as well as adjacent to the insertion site. The design of the device and use of the adhesive can allow for the formation of one or more barrier points that can inhibit and/or prevent microbes from entering into the insertion site. Also, the device and adhesive combination can provide one or more anti-microbial barriers that can inhibit propagation of the microbes that come into contact with the medical device, skin, or the like. A barrier point is formed by adhering skin to the device through the adhesive structure and/or with an optional anchoring suture so as to occlude the insertion site. This inhibits microbes from entering into and infecting the insertion site by forming a physical barrier at or adjacent to an incision in the skin where the catheter is percutaneously inserted through the skin.

The use of a device and adhesive can provide an impermeable barrier against the microbes that tend to infect catheters by contaminating the catheter at the site of skin entry and subsequently traveling down the external surface of the catheter and into the bloodstream. Importantly, the device and adhesive can be used without the need for many of the antimicrobials and antiseptics that are commonly employed, although these may also be added if desired. Current practices try to decrease the incidence of CRI by decreasing the bacterial load through antiseptics or antibiotics. However, CRI can now be inhibited or ameliorated by a method of using a composition and/or medical device as a barrier at a site where a medical device is inserted into skin. As such, the inventive composition and/or medical device can block access of the colonizing bacteria to the extra-luminal surface of the catheter at the skin-catheter interface. Also, such a method of using the inventive composition and/or medical device can be used in addition to current infection-reducing interventions. While the barrier device can be used in a manner that does not require the use of an antimicrobial composition, such antimicrobial compositions can be applied at various locations with respect to the barrier device and placement on the skin. For example, the antimicrobial composition, such as a traditional antibiotic or antiseptic (e.g., chlorohexedine, alcohols, quaternary ammonium compounds, boric acid, chlorohexedine gluconate, iodine, etc.) somewhere like reservoir. The antimicrobial composition can be placed in substantially any place the adhesive can be placed. This can include the antimicrobial composition being deposited on a skin-contacting surface, medical device-contacting surface, or the like, or even may be impregnated into the barrier materials by using silver ions or other approaches as outlined in U.S. Pat. No. 5,779,687 and U.S. Patent Application Numbers 2004/0106912, 2010/0010086, 2009/0157000, and 2008/0279907, each of which are hereby incorporated by reference in their entirety. To this end, antimicrobials and antiseptics are normally not needed with the present invention because the inventive barrier can prevent primary contamination with microorganisms from taking place prior to any possible secondary infection related issues. In addition, the inventive barrier can eliminate issues of organism resistance that are commonly associated with the currently available antimicrobials and antiseptics. Thus, the device and adhesive can be advantageous in limiting the use of antimicrobials and antiseptics, and thereby reduce the onset or occurrence of drug resistant microbes.

Referring now to the drawings by numerals of reference, two illustrative embodiments of the improved catheter attachment apparatus in accordance with the present invention is designated as numeral 10, as seen in FIGS. 1a-1b and 2a-2c, both of which may be formed from a flexible (preferably clear) plastic elongated tubular piece with or without a flange portion at a bottom opening and with a seal at a top opening. One possible variant on the elongated tubular piece is that it may be formed from an accordion-style or profiled tubing that is capable of collapsing or expanding the length of the elongated tubular piece 18 according to the treatment needs of a given patient. With specific regard to FIGS. 1a-1b, the improved catheter attachment apparatus may comprise at least two separate, interlocking portions, namely an upper portion 10a, and a lower portion 10b. This variant of the present invention is useful for situations where the closed space (e.g., the catheter 1 and/or the insertion site 22) that results from the present system and method needs to be accessed for any of several medical reasons, such as for adjusting a catheter. An elongated tubular piece 18 with the below described interlocking system particulars is provided for, so as to maintain sterility integrity while providing for ready access therein.

Typically, the elongated tubular piece 18 may have the opening at the lower end of the elongated tubular piece 18 situated over a 22, located on the skin of a patient, which will be situated a medical professional inserts a catheter 1 at 22. In doing so medical professional will normally insert the catheter 1 at catheter insertion site 22 after having inserted a lumen of catheter 1 along the length of upper and lower portions 10a and 10b, through the conduit there in each piece which exists by virtue of the elongated tubular piece 18 being hollow. Note that upper and lower portions 10a and 10b can be slid down the length of the lumen of catheter 1 so as to situate lower portion 10b, and thereafter interlocking upper portion 10a about the catheter insertion site 22. Although the interlocking portions 10a and 10b may be affixed to each other in many different fashions, in one possible embodiment (depicted therein), the upper portion and a may have an interlocking notch 15 which can cooperatively interface with a locking groove 13 so that the upper portion 10a and the lower portion 10b may be frictionally engaged by inserting a slightly smaller diameter upper portion 10a concentrically within the slightly larger diameter lower portion 10b and locking the two relative to each other through the aforementioned interlocking notch 15 and locking groove 13. Thereafter the adhesive structure 12 may be shaped in many different square or disk shaped profiles (with or without a slit as depicted in FIG. 2), with a center hole cut out so that it may be applied around the lower portion 10b so as to concentrically overlap perpendicular flange 10c, and so as to spread out from the flange on to exposed skin surrounding catheter insertion site 22. In one embodiment a seal 14 will be frictionally engaged with the opening at the upper portion of the elongated tubular piece 18 once the lumen of catheter 1 has been inserted through the length of seal 14. Note that seal 14 may take many different embodiments and by way of illustration only, one particular embodiment may be seen as depicted in FIGS. 1a-1b and FIGS. 2a-2c as being formed from a modified tubular plastic piece, with or without a flange for gripping, and having (in one illustrative embodiment) a threaded engagement (not specifically depicted) for screwing tight and locking within the opening of the upper portion of elongated tubular piece 18. To this end, seal 14 may normally have a diameter that is substantially narrowed at the upper portion 14a such that when the lumen of catheter 1 is inserted through the length of seal 14, the diameter is such that it will frictionally seal off any possible gaps existing between the diameter of the lumen of catheter 1 and the diameter at upper portion 14a. This seal may be further augmented by having a flexible rubber aperture or gasket (not depicted) situated within the narrow confines of 14 for forming a physical barrier to microbial entry along the length of the lumen, and/or may alternatively include a medical tape wrapped around the interface of the lumen and the narrow entry at upper portion 14a. By applying the seal and adhesive structure to the aforementioned catheter attachment apparatus over a catheter, it results in a closed space that holds the catheter in it, such that as long as the space is kept closed, catheter 1 and insertion site 22 inside are protected from becoming contaminated and will remain free from any infection.

With specific regard to FIGS. 2a-2c, the improved catheter attachment apparatus 10 may exhibit all of the above described structural aspects but with and alternatives structure that instead comprises only one single integral piece that forms elongated tubular piece 18. In either case, the length of the elongated tube structure that covers the catheter may range between 1-50 cm in length, but optimal lengths may vary between 10-30 cm long when expanded from collapsed accordion style (FIG. 2b) to full elongation (FIG. 2c). The diameter of the elongated tube structure may range between 1-8 cm in length, but optimal diameters may vary between 1.5-5 cm long. The surface area of the skin around the catheter insertion site covered by the illustrative tape portion (e.g. adhesive structure shown in 2a) will vary greatly, but will generally provide for diameters in the range of 5-30 cm (if disc shaped), or the equivalent if square, rectangular, or otherwise shaped.

As seen in FIGS. 3a-b, the closed space made by the above described embodiments with the screwable seal catheter capability, more active antiseptic measures such as evacuation of air/oxygen out of the space (vacuum packing), irrigation with antiseptic solution, or filling with biologically inactive gases such as carbon dioxide (generally more desirable than nitrogen or helium because of the smaller likelihood of gas embolism) may be provided for by including portable holes or insertion windows on the elongated tubular piece 18 so as to provide for vacuum suction or gas filling of the empty space within the conduit 19, known approaches in the art for gas filling or vacuum technologies utilizing, three-way stop cocks or fluid irrigation inlets and outlets 3. Given the seal of nature in the above described embodiments, using a sealed gas chamber or fitment (e.g., vacuum/gas), or irrigation fitment can serve to reduce the possibility of microbial growth within the closed space of conduit 19.

Additionally, it is understood that an indwelling catheter may need to be secured, given that catheters can easily be pulled out of the body inadvertently. One of the best ways to secure a catheter is to use a suture to secure the catheter down onto the skin of the patient. However there are problems with using sutures to secure a catheter to skin. Specifically, a catheter could be sutured by itself, however, the surface of it needs to be smooth so it can be atraumatically inserted into the body, but a sufficient amount of traction may not be able to be generated on the catheter surface with a suture. Conversely, if tied too tightly, the suture can compromise the lumens of the catheter. Moreover, bulky adaptors and the like used in this process can create a condition to favor microorganism growth around them under a plastic tape used in the prior art. One possible solution for the problem is provision of an anchoring suture fitment or structure as depicted in FIG. 4, wherein a suture 20, 21 may be tied so as to further buttress the whole arrangement (not depicted). Further to this point, use of an anchoring suture is possible through the use of anchoring or tying the suture to an eyelet, window or other means for securing (not depicted). The same suture 20, 21 can then also be tied onto the skin at 22 to further anchor the catheter (not depicted). In practice though, the sutures should not be left too long before installing the inventive catheter attachment apparatus, given a hypothetical possibility of immediate colonization of microorganisms around the above sutures before they become sequestered and closed within the conduit of elongated tubular piece 18. In further practice, the second anchoring suture may also be tied to the lumen of catheter 1 (not depicted). In any case it is important to note that the second anchoring suture should have no overlapping with the catheter attachment apparatus and should ideally not include any dressing tape on it. If the catheter insertion site and the second anchoring suture site are covered with the same dressing material (such as tape), this will result in violation of the sterility integrity, namely inadvertent contamination of the catheter leading to infection, or possibly even more serious morbidity, such as sepsis.

The above-described cylinder like or tube based embodiments may normally be easier to use in practice, however, the present invention also provides for an additional embodiment that may be workable in time-limited situations, yet still provides for the high standard of quality that is nevertheless required in real clinical settings. Whereas the cylinder like tube based embodiments offer ease of access to the closed-off catheter and insertion site 22, it does need to be preloaded around a catheter during the catheter placement process, by contrast, the segmented matching flexible strip method and apparatus described below can be applied after placement/insertion of a catheter. There are additional benefits to using the alternative embodiment described as the segmented matching flexible strip approach. For example, with certain patients it may at times be required to change the catheter attachment apparatus for adjustment purposes or other reasons, and with the cylinder like tube based approach described above, the catheter needs to be removed in order to exchange or adjust the catheter. However, when but using the segmented matching flexible strip method described below, the old cover/attachment apparatus can easily be cut to open with sterilized scissors or the like to remove the catheter attachment apparatus from the catheter. Moreover, the segmented matching flexible strip approach can easier to apply in emergency situations.

As illustratively shown in FIGS. 5*a*-5*b*, the segmented matching flexible strips may be formed from Mylar, metallic foil, or any type of flat, flexible plastic or non-plastic materials. To this end, in one illustrative embodiment, the segmented matching flexible strips may be formed from clear vinyl films substantially identical in the shape or profile, and with dimensions that may be akin to those described above for the tube based embodiments. An important aspect of segmented matching flexible strip approach is the segmented adhesive areas (also called adhesive structure) disposed on each respective flexible strip. The adhesives may, in one alternative embodiment, be provided according to known approaches for adhering bandages to human skin, but are also augmented with anti-microbial preparations as described elsewhere in this specification. Nevertheless, the adhesive applied thereon is structured so as to provide for segmented release liners in the discrete application of the keys of onto the surface area covered by said release liners. Instead of merely providing for a total adhesive surface on one or both of the matching flexible strips and having a release liner backing throughout, at least one of the flexible matching strips will have adhesive that has been applied at least to the perimeter surface areas around the edges of the given strip so as to improve the efficacy of adhesion in practice upon the lumen of a catheter. By way of illustration only, in FIG. 5*a* (only one matching half or portion, 10' of) the adhesive is depicted as having been applied during the manufacturing process of the flexible matching strip only to the edge areas so as to prevent inadvertent, premature adhesion directly to the lumen, as the provision of such otherwise could hamper the keys of application because the over-application of adhesives may tend to make the flexible matching strip stick to too many things at once. To this end, the areas that are treated with adhesive may be segmented according to various approaches but in the illustrative embodiment depicted in FIG. 5*a* may have a separate segment of adhesive at area 24 and by way of further example to additional segmented areas of adhesive at length 25 and length 26. The reason for segmenting these adhesive areas is so as to further augment the concept of limited adhesive usage which will make the matching flexible strips easier-to-use in practice. The reason the strips will be easier to use and practice with segmented adhesive areas is because a medical professional or other user can sequentially and selectively remove separate release liners that cover the adhesive before adhesion usage, so as not to have one unwieldy, sticky adhesive strip (e.g., similar to that of a long strip of tape that gets tangled up from hearing upon itself and other surfaces for which it was not intended to stick to) that will inadvertently stick to undesired areas including the user's fingers, other medical equipment, and non-target areas of the patient's skin. Thus for example, the user can begin the application of the segmented matching flexible strips by taking one flat strip (e.g., on half of the matching portions, 10') depicted as 10' in FIG. 5*a*, and can release the liner covering the adhesive area portion at 24. The user can then begin sticking just the adhesive portion area 24 to the surface of the catheter 1, and can begin preparing the proper alignment of the lumen throughout the length of the segmented matching flexible strip 10'. Note that for any given illustrative area(s) during the course of application of the same where the adhesive portion has not yet, in the sequence of serially peeling off the non stick backing from the adhesive areas been applied at 27, will help avoid unnecessary sticking of the segmented matching flexible strip 10' tube to either the fingers of a medical professional during the course of a harried, emergency procedure and/or from sticking to the length of the catheter before it has been properly aligned longitudinally along the length of the matching flexible strip 10'. Thereafter, the user can take off one lengthwise strip 25, and then another lengthwise strip 26, one by one so as to mate up, in a properly aligned fashion, one matching flexible strip 10' and the other matching flexible strip 10", thereby mating up the completed matching flexible strips together, as seen in FIG. 5*b*. Thereafter, the user may affect one or more segmented adhesive areas 31, 32 to the skin of the patient and the similarly selective fashion, for both respective matching flexible strips 10', 10". Note that in additional embodiments, the matching strips may be imprinted with alignment indicia so as to better guide the user as to where to align the lumen of the catheter and where to apply the segmented adhesive areas 31, 32 as flaps against the patients skin. Further note that the difference between 10' and 10" may, in certain embodiments, entail differences in the pattern of adhesive applied onto the films. For example, one matching flexible strip may have the adhesive applied in the segmented surrounding (perimeter) patterns 24, 25, 26 as well as one or two segmented adhesive areas 31, 32. On the other hand, the other matching flexible strip may be such that the adhesive is applied only at the top (adhesive area portion 24) and at the bottom skin contacting portions such as the one or more segmented adhesive areas 31, 32. Provision of such will help ensure that in clinical settings, matching flexible strips will not stick to what they are not supposed to in the course of usage, but instead will form a protective wrapping around the lumen of a catheter and will also adhere to the patient's skin around the insertion site of the lumen of the catheter, in such a way so as to completely seal off, as a physical barrier to microbial entry at or near the catheter insertion site. Thus, there whatever the exact adhesive application and segmentation of the two matching flexible strips 10' and 10", the provision of both is such that they are substantially identical in the shape, but one is covered with adhesive in most of its surface area (or its perimeter surface area), and the other is adhesive free in most of its surface area except for the top and the bottom of the part as described above.

In one embodiment, it may be more useful to reverse the above-described procedure according to the following order. First, the release liner of area 31 of the first matching flexible strip 10' may be peeled off and the adhesive flap thereof is placed onto the catheter with, say, an illustrative red edge line 37 (such as one part of the above described illustrative alignment indicia) being printed thereon regarding the placement thereof, so as to situate the same close enough yet not too far away from the catheter insertion site. Then the release liner of area 32 is removed to place the adhesive flap more firmly. Then the first matching flexible strip 10' and the catheter are lifted up with the tape being folded at the red edge line to form a roughly perpendicular alignment against the patient's skin. Thereafter, the non stick backing (e.g., release liner) of adhesive area 24 may be peeled off so that adhesive area 24 may be situated so as to wrap the catheter at the top of the first matching flexible strip 10', with the non stick backing of adhesive areas 25, 26 subsequently being peeled off sequentially as the second matching flexible strip 10" is—after any release liners (if applicable) on it are also removed—mated in approximate alignment there with. Provision of such will therefore more accurately wrap the catheter at the same place that it is inserted because of the alignment of the first matching flexible strip 10' proximate to the catheter insertion site. Accordingly, performance of the above steps will complete the whole assembly of one alternative embodiments of the system, and will therefore provide a secure seal between the two matching flexible strips 10', 10" all along the entire perimeter areas 24, 25, 26 and at the area proximate to the catheter insertion site on the patient's skin.

After all of the above has been properly placed, all of the intubation instruments can then be, in one embodiment, applied as a method of using a barrier device in combination with an adhesive, including those that contain a cyanoacrylate, in order to form an impermeable barrier against bacteria at a percutaneous incision site for passing a medical device into or through skin. As such, the device and adhesive are placed at the incision so as to contact the skin and barrier device so as to form a barrier. Also, the adhesive can be used to form barriers between the barrier device and medical device as well as between the skin and medical device in order to provide one or more barriers as described. The one or more barriers can retain the medical device in a static position relative to the skin and incision such that a barrier inhibits bacteria from entering the incision. Bacteria tend to infect catheters by contaminating the catheter at the site of the percutaneous incision and subsequently traveling down the external surface of the catheter and into the bloodstream. Thus, the one or more barriers formed with the barrier device and adhesive can both provide a static medical device position as well as provide a barrier that inhibits microbial infections in the incision. The present system could optionally be augmented through the use of antimicrobial coatings or materials that are formed or impregnated with antimicrobial properties (e.g., such as impregnated or coated vinyl/plastic using chlorohexedine, silver ions, etc.). By way of just one example, one may impregnate or coat all of the materials used in the attachment with antimicrobial additives as discussed above. Or just certain portions of the catheter or catheter attachment apparatus near the opening of the elongated tube structure, the seal, and/or near the catheter insertion site. However, it is noted that generally, indwelling catheters should not be made of any antiseptic chemicals (chlorohexedine, betadine, etc.) because of the possible direct toxicity against the host. On the other hand, for catheter applications which always stay outside the human body can certainly contain antimicrobial chemicals to augment the physical anti-microorganism (barrier) properties of the present invention.

In any of the above various embodiments, the applications thereof on a patient may typically involve some of the following steps. First, one might prepare the skin around the catheter insertion site 22 thoroughly with an antiseptic solution, with chlorohexedine being preferred to betadine most of the time. When inserting the catheter, it is helpful to minimize bleeding in association with the procedure, as blood is a well known culture media and can contaminate the surgical procedure field, the procedure equipment, and/or the catheter placement tray. This may be augmented by avoiding the use of a scalpel when cutting the skin after placing the guide wire, and by using a needle such as an 18G-type instead of a scalpel whenever possible, preferably with a narrow dilator. Similarly, it is helpful not to insert the catheter too deep and/or pull back, as the catheter may become contaminated with blood or body fluid. After catheter placement, one should normally wipe down any blood and/or flush any lumens of the catheter that may remain in the surgical procedure field. In general, it is preferable to let the skin and the catheter dry completely before applying the inventive system described herein.

The inventive technology can be applied to virtually all types of the indwelling catheter, whether an intra-arterial catheter, a single lumen indwelling catheter, or a central venous catheter (including those with double or triple lumens). More importantly, the present invention may also be used with a Foley (urinary tract based) catheter. For example, with male patients, the adhesive structure of the above described embodiments may be modified with additional radial slits for adhering to the corona of male genitalia, or may be shaped so as to adhere in a dome-shaped (rather than flat) fashion, or even may be replaced with a condom like material for adhering in a column shaped adhering portion. In the case of female patients, areas around the catheter insertion site skin may need some modification in its shape in order to tailor to their anatomy, such as applying a triangle-shaped smaller and possibly thicker gel-type adhesive onto the skin region around the Foley catheter insertion site at the urethral opening so the elongated tubular piece of the device can be held with sufficient sterility integrity even in the inside of the female genitalia.

While this invention has been described fully and completely with special emphasis upon preferred embodiments, it should be understood that within the scope of the appended claims the invention may be practiced otherwise than as specifically described herein. The present invention may be therefore embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope. All references (e.g., journal articles, published patent applications, patents, websites, and the like) that are recited herein are incorporated herein by specific reference in their entirety.

I claim:

1. An improved catheter attachment apparatus for reducing infections associated with a catheter, said improved catheter attachment apparatus comprising:

an elongated tube structure having a bottom end and a top end and a tube conduit extending from an opening at said top end to an opening at said bottom end for receiving a length of a lumen of a catheter, said elongated tube structure being further provided with a perpendicular flange at said bottom end, wherein said elongated tithe structure further includes insertion windows at said top end and at said bottom end, said insertion windows providing for gas filling and vacuum packing of the empty space within said tube conduit, said insertion windows further including at least one three-way stop cock;

a seal attached to said top end of said elongated tube structure, said seal being configured for receiving said lumen of said catheter and forming a physical barrier to microbial entry at said top end of said elongated tube structure, said seal further comprising:

a narrowed opening at a top end of said seal for receiving said lumen of said catheter and for sealable engagement with said lumen of said catheter thereby;

a widened opening at a bottom end of said seal, said widened opening being in concentric frictional engagement with said opening at said top end of said elongated tube structure;

and a seal conduit, said seal conduit extending from said narrowed opening, to said widened opening, for passing through of said lumen of said catheter from said narrowed opening to said widened opening, and for passing through of said lumen of said catheter at said opening at said top end of said elongated tube structure, into said elongated tube structure;

an adhesive structure for adhering to said perpendicular flange at said bottom end of said elongated tube structure and for adhering to exposed skin surrounding a catheter insertion site, said adhesive structure having a center hole cut out for application around said bottom end and onto said perpendicular flange in a concentric overlap, and onto said exposed skin surrounding a catheter insertion site so as to spread out from said concentric overlap of said perpendicular flange, said adhesive structure having segmented areas of adhesive with separate release liners for sequential, selective adhesion usage, said adhesive structure cooperatively forming with said perpendicular flange a physical barrier to microbial entry at said bottom end of said elongated tube structure and on said exposed skin surrounding a catheter insertion site.

2. The improved catheter attachment apparatus of claim 1, wherein said elongated tube structure is funned from a flexible, collapsible accordion profiled plastic tubing, and wherein:

said seal further includes a flexible rubber aperture situated within said narrowed opening of said seal, said flexible rubber aperture forming a narrowed diameter at said narrowed opening for sealing off any gaps between a lumen for a catheter and said narrowed opening; and wherein said seal, said elongated tube structure, and said adhesive structure together form a closed space for contamination protection; and wherein said adhesive structure is disk shaped with a slit and a concentric center hole cut.

3. The improved catheter attachment apparatus of claim 2, wherein said elongated tube structure is configured to be affixed at an insertion site to skin by said adhesive structure for adhering to said perpendicular flange at said bottom end of said elongated tube structure, and further includes an irrigation fitment for contamination protection around said insertion site, said irrigation fitment having antiseptic fluid irrigation inlets and outlets configured for antiseptic fluid irrigation of the empty space within said tube conduit.

4. The improved catheter attachment apparatus of claim 3, wherein said seal, said elongated tube structure, and said adhesive structure each include antimicrobial additives, said adhesive structure containing cyanoacrylate.

5. The improved catheter attachment apparatus of claim 4, wherein said antimicrobial additives are impregnated within plastic of said seal, of said elongated tube structure, and of said adhesive structure, said antimicrobial additives consisting of silver ions; and wherein said closed space for contamination protection is filled biologically inactive gases, said biologically inactive gases including at least carbon dioxide.

* * * * *